July 21, 1970 M. COMBE Plant Pat. 2,981
ROSE PLANT
Filed Sept. 18, 1968
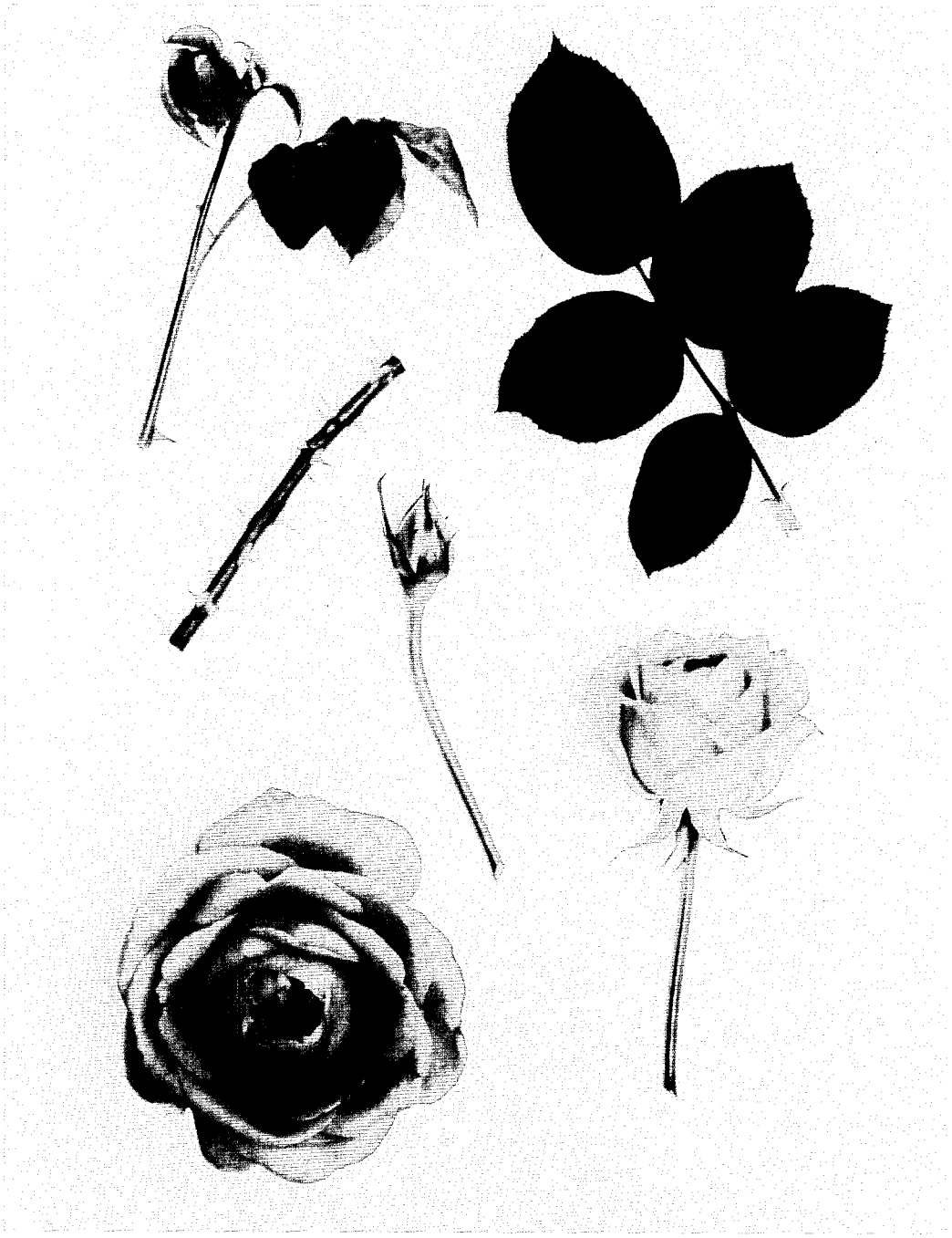
Inventor.
Maurice Combe
By: Robb & Robb
Attorneys.

United States Patent Office

Plant Pat. 2,981
Patented July 21, 1970

2,981
ROSE PLANT

Maurice Combe, St. Martin d'Heres, France, assignor to Jackson & Perkins Company, Newark, N.Y., a corporation of New York

Filed Sept. 18, 1968, Ser. No. 760,739
Int. Cl. A01h *5/00*
U.S. Cl. Plt.—21 1 Claim

The present invention relates to a new and distinct variety of rose plant of the hybrid tea class, which was originated by me by crossing the rose variety known as "Coup de Foudre" (unpatented) with the rose variety known as "Kordes' Perfecta" (U.S. Plant Pat. No. 1,604).

The primary objective of this breeding was to produce a new and improved rose variety which bears flowers of a novel color. This objective was fully achieved, along with other desirable features, as evidenced by the following unique combination of characteristics which are outstanding in the new variety and which distinguish it from its parents, as well as from all other varieties of which I am aware:

(1) An upright plant habit of average vigor; and (2) A distinctive, attractive and unusual flower color generally corresponding to Garnet Brown suffused with Nopal Red and Scarlet.

Asexual reproduction of my new variety by budding, as performed in France and at Newark, N.Y., and also at Pleasanton, Calif., shows that these characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new rose variety, with color terminology in accordance with Ridgway's Color Standards and Nomenclature except where general color terms of ordinary dictionary significance are obvious:

Parentage: Seedling.
*Seed parent.*—"Coup de Foudre."
*Pollen patent.*—"Kordes' Perfecta."

Class: Hybrid tea.

FLOWER (Observations made from specimens grown outdoors at Newark, N.Y., U.S.A., near mid-afternoon during the month of August.)

Blooming habit: Continuity—continuous; new flowers produced when spent blooms are cut throughout the summer.

Bud:
*Peduncle.*—Relatively stout; occasionally with a few thorns; usually smooth. Size—from 2½ inches to 3½ inches long. Color—Light Bice Green, Plate 17.
*Before calyx breaks.*—Size—from ¾ inch to 1 inch long. Shape—nearly ovoid, with pointed apex. Color—from Light Bice Green, Plate 17 to Bice Green, Plate 17.
*Sepals.*—Color—base Light Bice Green, Plate 17, darkening to Forest Green, Plate 17. Length—about ¾ inch. Edge—from nearly smooth to lined with small glands; small appendages; with foliaceous tips on flowers borne on large canes.
*Petal color (as sepals separate).*—From Oxblood Red, Plate 1 to Carmine, Plate 1.

Bloom:
*Opening flower.*—Shape—generally round, with center petals relatively short. Size—from 1½ inches to 1¾ inches long; approximately equal width.
*Open flower.*—Shape: outer petals—slightly recurved at tips; inner petals incurved until full blown, displaying flower parts. Size—from 3 inches to 3½ inches.
*Petals.*—Shape—nearly round. Quantity—from 35 to 45 petals. Substance—medium thickness and rigidity. Color: Newly open—upper surface—varies from tip to base from Garnet Brown, Plate 1, through Nopal Red, Plate 1, to a color between Brazil Red, Plate 1 and Scarlet, Plate 1, with an irregular spot of Barium Yellow, Plate 16 at point of attachment; reverse surface—Scarlet Red, Plate 1. Three-days open—Nopal Red, Plate 1, shaded heavily with Bordeaux, Plate 12.
*Petaloids.*—Several. Color—same as petals.
*Persistance.*—Petals remain on plant 5 or 6 days after opening and then drop off.
*Fragrance.*—Very slight. Nature—tea rose.

REPRODUCTIVE ORGANS

Stamens: Arranged in orderly ring around outer edge of receptacle; uneven in length.
Filaments: Color—Spectrum Red, Plate 1.
Anthers: Color—Maize Yellow, Plate 4 in center, with Light Cadmium Yellow, Plate 4 on edges.
Styles: Irregular in length; thin; in cluster from center of receptacle. Color—white when young, aging to Eosine Pink, Plate 1 when mature.
Stigmas: Color—Baryta Yellow, Plate 4.
Ovaries: Enclosed in receptacle.

PLANT

Habit: Upright bush habit; lateral branches grow vertically; average vigor.
Foliage:
*Leaves.*—Usually 5 leaflets; above average abundance.
*Leaflets.*—Shape—broadly elliptical. Edge—serrated, with small single serrations. Apex—bluntly pointed. Surface—semi-glossy. Color: upper surface—Varley's Green, Plate 18; lower surface—Light Hellebore Green, Plate 17.
*Rachis.*—Lower side—with several recurved thorns; color—Light Lumiere Green, Plate 17. Upper side—color—Claret Brown, Plate 1, suffused with Light Lumiere Green, Plate 17.
*Stipules.*—Color—slightly lighter than leaflets. Size—small. Edge—glandular. Points—slender.

Stems:
*New stems (with flower developed).*—Generally smooth. Color—Grass Green, Plate 6.
*Old wood.*—Smooth. Color—from Grass Green, Plate 6 to Cedar Green, Plate 6.
New growth: Color—Garnet Brown, Plate 1, suffused with Light Green.
Thorns: All large size; from few to many; long base; narrow width; points curved downward slightly. Color: mature—Russet, Plate 15; young—somewhat lighter than mature thorns.

I claim:

1. A new and distinct variety of rose plant of the hybrid tea class, substantially as herein shown and described, characterized particularly as to novelty by the unique combination of an upright plant habit of average vigor, and a distinctive, attractive and unusual flower color generally corresponding to Garnet Brown suffused with Nopal Red and Scarlet.

No references cited.

ROBERT E. BAGWILL, Primary Examiner